United States Patent
Antonucci et al.

(10) Patent No.: US 6,177,534 B1
(45) Date of Patent: Jan. 23, 2001

(54) SILYLATED RESINS AND THE SYNTHESIS THEREOF

(75) Inventors: Joseph M. Antonucci, Kensington; Jeffrey W. Stansbury, Frederick; Bruce O. Fowler, Baltimore, all of MD (US)

(73) Assignee: The United States of America as represented by the Secretary of Commerce, Washington, DC (US)

( * ) Notice: Under 35 U.S.C. 154(b), the term of this patent shall be extended for 0 days.

(21) Appl. No.: 09/213,892

(22) Filed: Dec. 17, 1998

Related U.S. Application Data (60) Provisional application No. 60/068,535, filed on Dec. 23, 1997.

(51) Int. Cl.$^7$ .................................................. C08G 77/14
(52) U.S. Cl. ................................. 528/26; 528/28; 528/29; 556/418; 523/116; 260/998.11
(58) Field of Search ................... 528/26, 28, 29; 556/418; 523/116; 260/998.11

(56) References Cited

U.S. PATENT DOCUMENTS

| | | | |
|---|---|---|---|
| 3,860,556 | 1/1975 | Taylor | 523/116 |
| 4,197,234 | 4/1980 | Temin | 523/116 |

(List continued on next page.)

* cited by examiner

*Primary Examiner*—Robert Dawson
*Assistant Examiner*—Kuo-Liang Peng
(74) *Attorney, Agent, or Firm*—Stevens Davis Miller & Mosher

(57) ABSTRACT

A silylated resin suitable for use as an adhesive binder for composites and in sealant and adhesive dental applications is represented by the general formula (I):

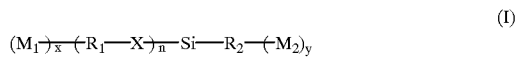

(I)

in which:
- $R_1$ is an aliphatic, cycloaliphatic, aryl, hydrocarbon, or fluorocarbon group;
- $R_2$ is the same as $R_1$ or a different aliphatic, cycloaliphatic, aryl, hydrocarbon, or fluorocarbon group;

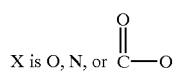

X is O, N, or $\overset{\overset{O}{\|}}{C}\!-\!O$

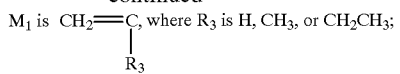

$M_1$ is $CH_2\!=\!\underset{\underset{R_3}{|}}{C}$, where $R_3$ is H, $CH_3$, or $CH_2CH_3$;

$M_2$ is the same as $M_1$ or a different functional or nonfunctional group selected from the group consisting of:

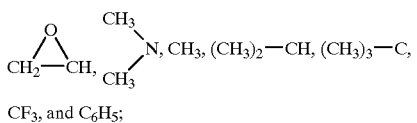

$CF_3$, and $C_6H_5$;

n is 1–3;
x is 1–20; and
y is 1–20;

which comprises the reaction product of the exchange reaction of a hydroxylated, aminated, or carboxylated acrylic resin represented by the general formula (II):

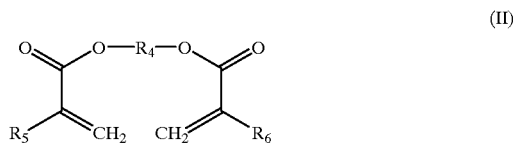

(II)

in which:
- $R_4$ is an aliphatic, cycloaliphatic, aryl, hydrocarbon, or fluorocarbon group with one or more protic functional groups selected from the group consisting of:

OH, N—H, and $CO_2H$

- $R_5$ is H or $CH_3$; and
- $R_6$ is H or $CH_3$;

with a trialkoxyorganosilane or triacyloxyorganosilane represented by the general formula (III):

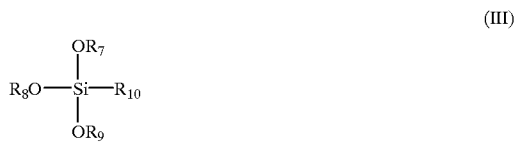

(III)

in which:
$R_7$, $R_8$, and $R_9$ each is:

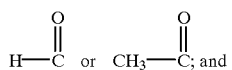

$R_{10}$ is an aliphatic, or aryl group which can optionally be substituted with a group from the group of an acrylic group, a methacrylic group, an epoxy group, and a substituted amino, hydroxyl, or carboxylic acid group such as an ester or an amide.

24 Claims, 2 Drawing Sheets

U.S. PATENT DOCUMENTS

| | | | |
|---|---|---|---|
| 4,308,014 | 12/1981 | Kawahara et al. | 523/115 |
| 4,504,231 * | 3/1985 | Koblitz et al. | |
| 4,595,598 | 6/1986 | De Luca et al. | 433/10 |
| 4,681,538 | 7/1987 | DeLuca et al. | 433/9 |
| 4,707,504 | 11/1987 | Walkowiak et al. | 523/109 |
| 4,806,381 | 2/1989 | Engelbrecht et al. | 427/2.26 |
| 5,071,933 | 12/1991 | Muller et al. | 526/304 |
| 5,112,884 | 5/1992 | Hanke | 523/116 |
| 5,192,815 | 3/1993 | Okada et al. | 523/115 |
| 5,241,081 | 8/1993 | Muller et al. | 549/232 |
| 5,294,646 | 3/1994 | Muller et al. | 523/120 |
| 5,380,901 | 1/1995 | Antonucci et al. | 556/440 |
| 5,453,530 | 9/1995 | Byerley et al. | 558/252 |
| 5,670,657 | 9/1997 | Kojima et al. | 549/39 |
| 5,739,245 * | 4/1998 | Lubbers et al. | 528/28 |

SILYLATED RESINS AND THE SYNTHESIS THEREOF

The present application claims priority of U.S. Provisional Patent Application Ser. No. 60/068,535, filed Dec. 23, 1997, and incorporated herein by reference.

BACKGROUND OF THE INVENTION

1. Field of the Invention

This invention relates generally to silylated resins and methods for preparing and using the same. The invention relates more specifically to silylated resins which exhibit a strong affinity for glass substrates, and which on polymerization yield strong, tough materials, suitable, for example, as dental restorative composite compositions, and in industrial applications as structural composites, caulks, adhesives, sealants, and coatings.

2. Discussion of the Prior Art

Polymeric dental composites have found increasing use in restorative dentistry. Because of their limited strength, toughness, and durability, however, such dental composites have been used primarily for restoring defective tooth structure that is not subject to high levels of masticatory stresses, e.g., anterior teeth rather than the occlusal areas of posterior teeth. Although currently used composites are not inherently adhesive to tooth structure, they are capable of being bonded to tooth structure via the prior application of an adhesive system.

The base monomer compound 2,2-bis-[4-(2'-hydroxy-3'-methacryloxypropoxy)phenyl]propane ("Bis-GMA") is widely used in dental composites, sealants, and adhesives. A disadvantage of Bis-GMA, however, is its high viscosity due mainly to the presence of its two hydroxyl groups. The hydroxyl functionality also enhances the water absorptivity of the Bis-GMA polymer, which can promote plasticization of the polymeric matrix and also compromise the critical interfacial phase of dental composites. Because Bis-GMA and similar dental resins do not adhere strongly to the glass fillers used with conventional dental composites, silane coupling agents such as the polymerizable trialkoxyorganosilane, 3-methacryloxypropyltrimethoxysilane ("MPTMS"), are used as surface treatment agents so that the siliceous fillers can be bonded to the polymer matrix and, thereby, reinforce the weaker organic phase of the composite and provide a mechanism for stress transfer from the lower modulus matrix to the higher modulus filler phase.

In order to provide a dental restorative composite possessing improved mechanical properties, especially wear or abrasion resistance, the addition of a polyfluorocarbon or polychlorofluorocarbon resin to a conventional inert inorganic filler used in combination with conventional liquid polymerizable binder systems are disclosed in U.S. Pat. No. 4,197,234 to Temin, and in Venz and Antonucci, *J Dent. Res.* 65, 183 Abstract 191 (1986). The inclusion of coupling agents to enhance the adhesion between the polymerizable resin binder and the filler are also disclosed. These references indicate that the filler particles are either pretreated with a silane coupling agent prior to blending the filler and liquid polymerizable matrix, or that the agent can be added to the polymerizable resin binder prior to addition of the inorganic particulate filler. In either method of silanization, however, the objective is to surface modify the filler phase, and not to modify the resin by silyl ether formation (by a silylation exchange reaction).

U.S. Pat. Nos. 5,071,933, 5,241,081, and 5,294,646 to Muller et al. all describe the development of adhesive resins for bonding to collagenous tissues, especially dentin. In U.S. Pat. No. 5,071,933, for example, the hydroxylated product is silylated to yield a trimethyl silyl derivative for mass spectrometric analysis. As in the aforementioned U.S. Pat. No. 3,860,556, however, the use of the monofunctional trimethylsilyl reagent is to enhance the volatility of the product, and thereby, facilitate its analysis. Trimethylsilylation is also used for analytical purposes in U.S. Pat. Nos. 5,241,081, and 5,294,646 in order to render certain reaction products sufficiently volatile for characterization by mass spectrometry.

The aforementioned silane-derived interfacial phase can be vulnerable to hydrolytic degradation, especially if the matrix and the interface allow significant absorption and transport of oral fluids. Therefore, there is a need to make the organic phases of the interface and the matrix of composites more resistant to the adverse effects of fluids in the oral environment.

The vinyl resin systems used in dental composites and related materials should ideally achieve on polymerization the contradictory goals of high conversion and minimal contraction. A high degree of conversion, with homogeneous network formation, is desirable because it maximizes the glass transition temperature of the matrix, thereby rendering it less susceptible to the softening effects of the oral environment, such as plasticization and degradation. Since polymerization shrinkage is directly correlated with conversion, a high degree of conversion can have undesirable consequences, such as the formation of gaps and stress sites in the composite and at the composite-tooth interface.

Base monomers such as Bis-GMA, with rigid molecular structures and high cohesive energy densities, require significant amounts of smaller, more flexible diluent monomers (e.g., triethylene glycol dimethacrylate) to yield resin systems with workable viscosities and matrices of relatively high degrees of conversion and glass transition temperatures. Another deficiency of conventional Bis-GMA resins is that they have a propensity to form matrices that are excessively brittle, i.e., they lack toughness.

A potential method of minimizing polymerization shrinkage while maximizing the degree of conversion is to use less viscous monomers of greater bulk and flexibility than Bis-GMA. An alternate method is to modify Bis-GMA by exchange reactions such as silylation so that the ensuing polymers have these desirable properties.

The use of silylated resins in dental composites such as those derived from Bis-GMA can have several advantages over Bis-GMA type composites, including: 1) conversion of the hydroxylated resin in virtually quantitative yields to more hydrophobic silyl ether derivatives; 2) increase in the molecular size of the resin without a concomitant increase in viscosity (with some silyl derivatives a viscosity decrease occurs); 3) control of the adhesivity and crosslinking potential of the resin through selection of the composition of the reactants (mole ratio of silane agent to Bis-GMA) and the reaction conditions; and 4) formulation of the composites without the need for presilanization of the filler phase.

One study, Antonucci et al., *J. Dent. Res.* 65, 219, Abstract 451 (1986) describes the synthesis of such silylated resins. Thus, the reaction of Bis-GMA with monofunctional silanes such as 3-methacryloxypropyldimethyl chloro- or ethoxy-silanes under base catalysis yields the corresponding disilyl ether of Bis-GMA. The resultant tetramethacrylate exhibits a much lower viscosity than Bis-GMA despite its greater bulk (molecular weight of 880). It is expected from structure-property considerations that these silyl derivatives, and especially the ones described herein, will exhibit enhanced toughness, fatigue resistance, and hydrophobicity that will result in polymeric materials of improved durability and environmental resistance.

Hydrophobic dimethacrylate monomers derived from bisphenol A and analogs thereof have also been described in U.S. Pat. No. 3,860,556 to Taylor as a means of improving the dimensional stability of dental composites in the aqueous oral environment. The trimethylsilyl reagents employed in the derivatization are monofunctional, however, in the sense that they can react only once with a hydroxyl group.

SUMMARY OF THE INVENTION

It is an object of the present invention to provide silylated resins having potential for use as adhesive binders for composites, and in sealant and adhesive dental applications. The present invention advantageously employs multifunctional silanes such as alkyl or aryl trifunctional silanes, with good leaving groups attached to the silicon, such as $OCH_3$, $OCH_2CH_3$, $O_2CCH_3$, and $N(CH_3)_2$ and more specifically for example, trialkoxyorganosilanes such as trimethoxyorganosilanes, which can react once, twice, or three times with hydroxyl, amino, and carboxyl groups, as well as other protic functional groups, and thereby, yield a variety of resins.

Accordingly, the invention relates to a silylated resin represented by the general formula (1):

$$(M_1)_{\overline{x}}(R_1-X)_{\overline{n}}-Si-R_2-(M_2)_y \quad \text{(I)}$$

in which:

$R_1$ is an aliphatic, cycloaliphatic, aryl, hydrocarbon, or fluorocarbon group;

$R_2$ is the same as R or a different aliphatic, cycloaliphatic, aryl, hydrocarbon, or fluorocarbon group;

X is O, $NCH_3$, or $M_1$ is where $R_3$ is H, $CH_3$, or $CH_2CH_3$;

$M_2$ is the same as $M_1$ or a different functional or non-functional group selected from the group consisting of:

$CF_3$, and $C_6H_5$;

n is 1–3;

x is 1–20; and y is 1–20;

which comprises the reaction product of the exchange reaction of a hydroxylated, aminated, or carboxylated acrylic resin represented by the general formula (II):

in which:

$R_4$ is an aliphatic, cycloaliphatic, aryl, hydrocarbon, or fluorocarbon group with one or more protic functional groups selected from the group consisting of:

OH, N—H, and $CO_2H$ $R_5$ is H or $CH_3$; and

$R_6$ is H or $CH_3$;

with a trialkoxyorganosilane or triacyloxyorganosilane represented by the general formula (III):

in which:

$R_7$, $R_8$, and $R_9$ each is:

$R_{10}$ is an aliphatic, cycloaliphatic, or aryl group which can optionally be substituted with a group from the group consisting of an acrylic group, a methacrylic group, an epoxy group, and a substituted amino, hydroxyl, or carboxylic acid group such as an ester or an amide.

The present invention permits the facile synthesis of a wide variety of readily polymerizable silylated resins with a wide spectrum of properties. Because of the presence in many of these resins of pendant, readily-converted silyl functional groups, such as, silyl ether or silyl ester groups of the type shown below:

$R_3SiOCH_3, R_2Si(OCH_3)_2, RSi(OCH_3)_3,$ $R_3SiOC(O)CH_3, R_2Si(OC(O)CH_3)_2$ and $$RSi(O-C(O)-CH_3)_3$$

the resins can have unique adhesive properties. Representing a marriage of acrylic and silicone chemistries, the synthesis of these novel hybrid resins typically involves only one step and employs readily available reactants. Many of the self-adhesive resins can be utilized as coupling agents for siliceous and other fillers, and as the organic matrices of thermoset composites. Their unique structural characteristics lend themselves to the preparation of condensable dental composites characterized by enhanced strength and durability compared to currently available composites. These novel resins also can be designed to have minimal polymerization shrinkage, low water sorption, and excellent adhesion to glass and similar substrates.

BRIEF DESCRIPTION OF THE DRAWINGS

Other objects, features, and advantages of the present invention will become more fully apparent from the following detailed description of the preferred embodiments, the appended claims, and the accompanying drawings. As depicted in the attached drawings:

DESCRIPTION OF THE PREFERRED EMBODIMENTS

The present invention will be disclosed in terms of the currently perceived preferred embodiments thereof.

The present invention provides a silylated resin represented by the general formula (I):

$$(M_1)_x-(R_1-X)_n-Si-R_2-(M_2)_y \quad (I)$$

in which:

$R_1$ is an aliphatic, cycloaliphatic, aryl, hydrocarbon, or fluorocarbon group;

$R_2$ is the same as $R_1$ or a different aliphatic, cycloaliphatic, aryl, hydrocarbon, or fluorocarbon group;

X is O, $NCH_3$, or $C(O)-O$ $M_1$ is $CH_2=C(R_3)$, where $R_3$ is H, $CH_3$, or $CH_2CH_3$;

$M_2$ is the same as $M_1$ or a different functional or non-functional group selected from the group consisting of $$\underset{CH_2}{\overset{O}{\triangle}}CH, \quad \underset{CH_3}{\overset{CH_3}{>}}N, \; CH_3, \; (CH_3)_2CH, \; (CH_3)_3C,$$

$CF_3$, and $C_6H_5$;

n is 1–3;

x is 1–20; and y is 1–20;

which comprises the reaction product of the exchange reaction of a hydroxylated, aminated, or carboxylated acrylic resin represented by the general formula (II):

$$\underset{R_5}{\overset{O}{>}}\underset{CH_2}{\overset{O-R_4-O}{>}}\underset{CH_2}{\overset{O}{>}}R_6 \quad (II)$$

in which:

$R_4$ is an aliphatic, cycloaliphatic, aryl, hydrocarbon, or fluorocarbon group with one or more protic functional groups selected from the group consisting of:

OH, N—H, and $CO_2H$ $R_5$ is H or $CH_3$; and $R_6$ is H or $CH_3$;

with a trialkoxyorganosilane or triacyloxyorganosilane represented by the general formula (III):

$$R_8O-\underset{OR_9}{\overset{OR_7}{Si}}-R_{10} \quad (III)$$

in which:

$R_7$, $R_8$, and $R_9$ each is:

$CH_3, CH_3CH_2, CH_3CH_2CH_2, (CH_3)_2CH,$

$$H-\overset{O}{\underset{}{C}} \text{ or } CH_3-\overset{O}{\underset{}{C}}; \text{ and}$$

$R_{10}$ is an aliphatic, cycloaliphatic, or aryl group which can optionally be substituted with a group from the group consisting of an acrylic group, a methacrylic group, an epoxy group, and a substituted amino, hydroxyl, or carboxylic acid group such as an ester or an amide.

The invention is directed to silylation exchange reactions conducted at moderate temperatures of approximately 23–100° C., either with or without the presence of catalysts or solvents, between hydroxylated resins such as Bis-GMA with silane agents such as MPTMS. The viscosities of the resulting resins generally are equal to, or less than, the viscosity of the Bis-GMA.

The treatment of inorganic substrates such as silica glass, alumina, and other mineral fillers with silane agents such as MPTMS is commonly referred to as silanation. In this specification, the term "silylation" denotes the exchange reaction that occurs between the silane agent and an organic compound that has protic functional groups such as hydroxyl groups, carboxylic acid groups, or amine groups.

For example, as indicated below, one mole of Bis-GMA:

Bis-GMA reacts stoichiometrically with two moles of MPTMS:

to produce the monosilylated resin compound:

Other silylated products that can be synthesized as depicted below include cyclic dimers via di-exchange, linear oligomers via di-exchange, and branched products:

Branched product in which M is

For higher molecular weight silane agents with even longer carbon chain segments, such as 10-methacryloxydecyltrimethoxysilane, the viscosity of the silyl ether derivatives is still considerably less than that of Bis-GMA. The residual hydroxyl and silyl methoxy ether content are functions of both the initial composition of the reactants, the nature of the leaving group of the silane, and the reaction conditions of time of reaction, type of catalyst, and especially, temperature.

The same type of reaction can be conducted with other functional monomers, such as, for example, carboxylated monomers. In this second embodiment, for example, one mole of pyromellitic acid di-2-methacryloyloxyethyl ester ("PMDM"):

reacts stoichiometrically with two moles of MPTMS:

to form the corresponding silyl ester of PMDM:

The synthesis procedures described in these examples were successfully applied to yield MPTMS silylated resins from the following hydroxylated monomers:

2-hydroxy-1-methacryloxy-3-phenoxypropane

6F-Bis-GMA, and

Bis(1-methacryloxy-2-hydroxy-1', 3'-hexafluoro isopropyl)benzene in which M is

In addition, this general synthetic procedure was applied to mixtures of hydroxylated monomers, e.g., Bis-GMA plus P-hydroxyethylmethacrylate ("HEMA").

The same general synthesis was applied to carboxylic acid containing monomers such as PMDM and amine containing monomer such as t-butylaminoethyl methacrylate to produce silylated resins based on these types of functionalized monomers.

A variety of silanes can be utilized in the preparation of silylated resins. By utilizing the general procedure described in the example, silylated derivatives of Bis-GMA have been obtained in excellent yield (>90%) by employing the following silanes as coreactants with Bis-GMA: methyltriethoxysilane; n-propyltrimethoxysilane; n-decyltriethoxysilane; tridecafluoro-1,1,2,2-tetrahydrooctyltriethoxysilane; 3-methacryloxypropyltriethoxysilane; 3-methacryloxypropyltriacetoxysilane; and 10-methacryloxydecyltrimethoxysilane.

In addition, the synthetic procedure described in the example was successfully applied to the synthesis of silylated Bis-GMA resins when the silane coreactant was a tetraalkoxysilane such as tetraetboxysilane:

$(CH_3-CH_2O)_4Si$ or a dialkoxysilane such as 3-methacryloxypropylmethyldimethoxysilane:

Thus, other hydroxylated monomers, such as, for example, HEMA, as well as monomers with other types of active groups, such as, for example, COOH, also can be silylated with MPTMS. A wide spectrum of silylated resins, therefore, can be prepared through exchange reactions involving hydroxylated, aminated, carboxylated, and other protic types of functionalized monomers and oligomers.

These exchange reactions can be conducted in solvents, including diluent monomers, either with or without the presence of catalysts. Choice of the resin/silyl composition and reaction conditions can be used to design resins with controlled reactivity, hydrophobicity, and polymerization shrinkage.

The silylated resins combine the properties of both acrylic resins and coupling agents, thereby simplifying the preparation of glass or ceramic filled composites. For example, unsilylated glass fillers can be used directly in the formulation of sealants and composites. These resins can also be used with presilylated fillers to supplement and enhance interfacial bonding. Such resins and composites can be used directly as repair materials for composites, porcelain, sealants, and in a number of other adhesive applications.

Viscosity and shrinkage of the resins can be controlled by selection of the silylating agents. For example, long chain organosilanes will reduce both viscosity, hydrophilicity, and polymerization shrinkage. Strength and toughness are other properties that can be controlled by this technology.

EXAMPLE

Transetherification exchange reactions of Bis-GMA with MPTMS were investigated. Transetherifications of Bis-GMA (available from Esstech) and MPTMS (available from Aldrich Chemical) mixtures with mole proportions of 2:1, 1.5:1, 1:1, and 1:2 were conducted neat at 65° C. in open vials (or flasks equipped for removal of byproducts) for a duration of from 1 hour to 120 hours. All of the reagents were commercially available and were used without further purification. Some of the analogs of Bis-GMA were synthesized.

Commercially available silanes (Gelest, Inc.) which may be employed in the synthesis include, for example: include: acetoxymethyltriethoxysilane allyltrimethoxysilane; benzyltriethoxysilane; benzoyloxypropyltrimethoxysilane; (N,N-diethyl-3-aminopropyl)trimethoxysilane; ethyltriacetoxysilane; ethyltriethoxysilane; (heptadecafluoro-1,1,2,2-tetrahydrodecyl)triethoxysilane; methyltriethoxysilane; n-methylaminopropyltrimethoxysilane; methacryloxymethyltriethoxysilane; methacryloxypropyltrimethoxysilane; methacryloxypropyltriethoxysilane; vinyltrimethoxysilane; strylethyltrimethoxysilane; acetoxypropyltrimethoxysilane; 3-(n-allylamino)propyltrimethoxysilane; cyclohexyltrimethoxysilane; 2-(3,4-epoxycyclohexyl)ethyltrimethoxysilane; (3-glycidoxypropyl)trimethoxysilane; 3-(2-imidazolin-1-YL)propyltriethoxysilane; isobutyltrimethoxysilane; isooctyltrimethoxysilane; n-octyltriethoxysilane; n-octadecyltrimethoxysilane; n-propyltriethoxysilane; n-phenylaminopropyltrimethoxysilane; phenyltriacetoxysilane; tris(dimethylamino)phenylsilane; phenyltrimethoxysilane; p-tolyltrimethoxysilane; pentafluorophenylpropyltrimethoxysilane; (3,3,3-trifluoropropyl)trimethoxysilane; (tridecafluoro-1,1,2,2-tetrahydrooctyl)triethoxysilane; tetraethoxysilane; tetrakis(dimethylamino)silane; (3-acryloxypropyl)trimethoxysilane; 3-cyanopropyltriethoxysilane; 5,6-epoxyhexyltriethoxysilane; hexyltrimethoxysilane; diethylphosphatoethyltriethoxysilane; 5-(bicycloheptenyl)triethoxysilane; and norbornenyltriethoxysilane.

The extent of reaction was determined by characterization of the reaction products by both FTIR (Nicolet Magna 550 Spectrometer) and $^1$H NMR (JEOL-GSX270 Spectrometer) spectroscopies.

Figure 1:
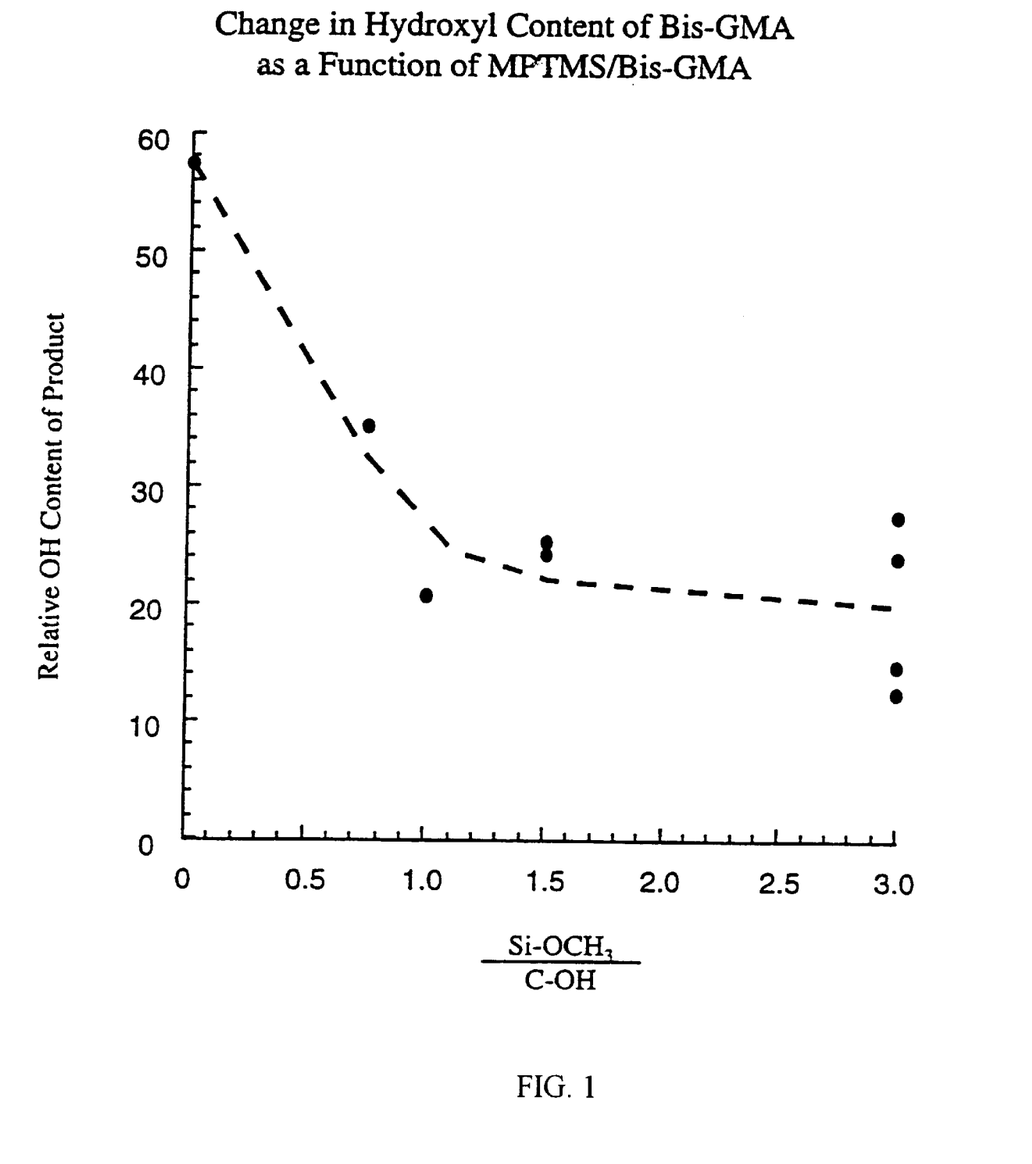
FIG. 1 is a plot of the relative OH content of the Bis-GMA product versus the mole ratio of the MPTMS/Bis-GMA reactant charge expressed as the ratio of $SiOCH_3/OH$.

As depicted in FIG. 1, the relative OH content of the Bis-GMA product versus the mole proportion of the MPTMS/Bis-GMA charge indicates that considerable conversion of the hydroxyl groups of Bis-GMA to the silyl ether products (see, e.g., FIG. 2) occurs and is dependent on the composition of the reactants.

Figure 2:
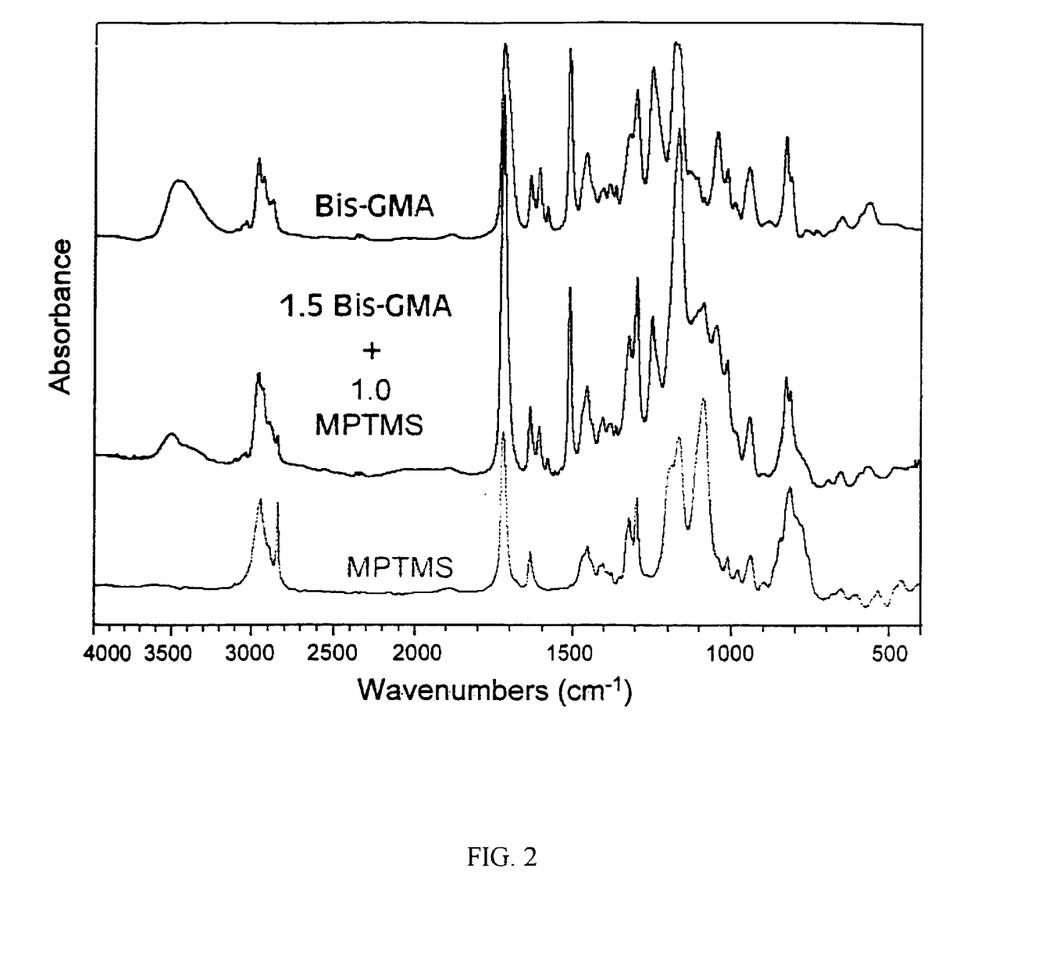
FIG. 2 shows the infrared spectra, absorbance versus wavenumber, for Bis-GMA, MPTMS, and the reaction product for a mole proportion of 1.5 Bis-GMA and 1.0 MPTMS.

As depicted in FIG. 2, analysis by FTIR indicated significant decreases in intensities of the band at 2842 $cm^{-1}$, $CH_3$ stretch of $CH_3OSi$ groups of MPTMS, and the presence of the broad band from about 3600 to 3100 $cm^{-1}$ due to OH groups of Bis-GMA (the band intensity changes were normalized to the Bis-GMA aromatic bands at 1608 $cm^{-1}$, 1582 $cm^{-1}$, and 1510 $cm^{-1}$). Analysis by $^1$H NMR confirmed the FTIR results.

The residual $SiOCH_3$ and OH contents of the silylated resin were determined to be primarily a function of the initial composition of the Bis-GMA and MPTMS charge, as well as a function of both the temperature and duration of the reaction.

The various silyl derivatives of Bis-GMA were photoactivated for visible light polymerization with camphorquinone and 4-ethyl dimethylaminobenzoate. Irradiations of thin films of some of these resins between crossed glass slides resulted in polymers that adhered tenaciously to glass and resisted debonding under tensile or shear mechanical stress.

As expected, chemical activation, e.g., benzoyl peroxide plus a polymerization accelerator, can also be used to effect polymerization.

The present invention, therefore, permits the facile synthesis of a wide variety of silylated polymerizable resins having a wide spectrum of properties. Reaction conditions can be modified so that these resins can have pendant, readily converted silyl ether groups, such as, for example,

This flexibility in methodology allows viscosity and adhesive properties to be controlled. The synthesis of these novel resins typically involves only one step and employs readily available reactants. Many of the self-adhesive resins can be utilized both as coupling agents for siliceous and other fillers, and as the organic matrices of thermoset composites. These novel resins also can be designed to have minimal polymerization shrinkage, lower stress development, low water sorption, and improved affinity for glass and similar substrates. Their unique structural characteristics lend themselves to the preparation of condensable dental composites that are stronger, tougher, and more durable than currently available composites.

These novel resins, because of their silyl ether or silyl ester structure, also have the potential to provide a self-healing mechanism if hydrolytic degradation occurs:

Hydrolysis of Silyl Ether Linkages

Siloxane Formation

Silanization

While only certain preferred embodiments of this invention have been shown and described by way of illustration, many modifications will occur to those skilled in the art and it is, therefore, desired that it be understood that it is intended herein to cover all such modifications that fall within the true spirit and scope of this invention.

What is claimed is:

1. A silylated resin represented by the general formula (I):

$$(M_1)_x\text{—}(R_1\text{—}X)_n\text{—}Si\text{—}R_2\text{—}(M_2)_y \qquad (I)$$

in which:
  $R_1$ is an aliphatic, cycloaliphatic, aryl, hydrocarbon, or fluorocarbon group;
  $R_2$ is the same as $R_1$ or a different aliphatic, cycloaliphatic, aryl, hydrocarbon, or fluorocarbon group;
  X is O, NCH$_3$ or $\overset{\text{O}}{\underset{\|}{\text{C}}}\text{—O}$;

$M_1$ is $CH_2=\overset{R_3}{\underset{|}{C}}$, where $R_3$ is H, CH$_3$, or CH$_2$CH$_3$;

$M_2$ is the same as $M_1$ or a different functional or non-functional group selected from the group consisting of:

CF$_3$, and C$_6$H$_5$;
  n is 1–3;
  x is 1–20; and
  y is 1–20;
  which comprises the reaction product of the exchange reaction of a hydroxylated, animated, or carboxylated acrylic compound represented by the general formula (II):

in which:
  $R_4$ is an aliphatic, cycloaliphatic, aryl, hydrocarbon, or fluorocarbon group with one or more protic functional groups selected from the group consisting of:
  OH, N—H, and CO$_2$H;
  $R_5$ is H or CH$_3$; and
  $R_6$ is H or CH$_3$;
with a silane selected from the group consisting of a trialkoxyorganosilane or triacyloxyorganosilane represented by the general formula (III):

in which:
  $R_7$, $R_8$, and $R_9$ each is:

CH$_3$, CH$_3$CH$_2$, CH$_3$CH$_2$CH$_2$, (CH$_3$)$_2$CH, $R_{10}$ is an aliphatic, cycloaliphatic, and aryl group which can optionally be substituted with a group from the group consisting of an acrylic group, a methacrylic group, an epoxy group, and a substituted amino, hydroxyl, or carboxylic acid group.

2. The resin of claim 1, wherein the hydroxylated acrylic compound is 2,2-bis-[4-(2'-hydroxy-3'-methacryloxypropoxy)phenyl]propane.

3. The resin of claim 1, wherein the carboxylated acrylic compound is pyromellitic acid di-2-methacryloyloxyethyl ester.

4. The resin of claim 1, wherein the trialkoxyorganosilane is 3-methacryloxypropyltrimethoxysilane.

5. The resin of claim 1, wherein the trialkoxyorganosilane is 10-methacryloxydecyltrimethoxysilane.

6. The resin of claim 1, wherein the trialkoxyorganosilane is 3-methacryloxypropyltriacetoxysilane.

7. The resin of claim 1, wherein $R_{10}$ is selected from the group consisting of an ester and an amide.

8. The resin of claim 1, wherein the hydroxylated acrylic compound is 2,2-bis-(4-(2'-hydroxy-3'-methacryloxypropoxy)phenyl)propane.

9. The resin of claim 1, wherein the carboxylated acrylic compound is pyromellitic acid di-2-methacryloyloxyethyl ester.

10. The resin of claim 7, wherein the trialkoxyorganosilane silane is 3-methacryloxypropyltrimethoxysilane.

11. The resin of claim 7, wherein the trialkoxyorganosilane silane is 10-methacryloxydecyltrimethoxysilane.

12. The resin of claim 7, wherein the trialkoxyorganosilane silane is 3-methacryloxypropyltriacetoxysilane.

13. The resin of claim 1, wherein X is O or and the one or more protic groups of $R_4$ are selected from the group consisting of OH and $CO_2H$.

14. A silylated resin represented by the general formula (I):

(I)

in which:
$R_1$ is an aliphatic, cycloaliphatic, aryl, hydrocarbon, or fluorocarbon group;
$R_2$ is the same as $R_1$ or a different aliphatic, cycloaliphatic, aryl, hydrocarbon, or fluorocarbon group;

X is O, $NCH_3$, or ;

$M_1$ is $CH_2=C$, where $R_3$ is H, $CH_3$, or $CH_2CH_3$;
   |
   $R_3$

$M_2$ is the same as $M_1$ or a different functional or non-functional group selected from the group consisting of:

$CF_3$, and $C_6H_5$;
n is 1–3;
x is 1–20; and
y is 1–20;
which comprises the reaction product of the exchange reaction of a hydroxylated, animated, or carboxylated acrylic compound selected from the group consisting of β-hydroxyethyl methacrylate, t-butylaminoethyl methacrylate and a compound represented by the general formula (II):

(II)

in which:
$R_4$ is an aliphatic, cycloaliphatic, aryl, hydrocarbon, or fluorocarbon group with one or more protic functional groups selected from the group consisting of:
OH, N—H, and $CO_2H$;
$R_5$ is H or $CH_3$; and
$R_6$ is H or $CH_3$;
with tetraalkoxysilane, dialkoxysilane, trialkoxyorganosilane or triacyloxyorganosilane, wherein said trialkoxyorganosilane or triacyloxyorganosilane is represented by the general formula (III):

(III)

in which:
$R_7$, $R_8$, and $R_9$ each is:
$CH_3$, $CH_3CH_2$, $CH_3CH_2CH_2$, $(CH_3)_2CH$, and $R_{10}$ is an aliphatic, cycloaliphatic, or aryl group which can optionally be substituted with a group from the group consisting of an acrylic group, a methacrylic group, an epoxy group, and a substituted amino, hydroxyl, or carboxylic acid group.

15. The resin of claim 14, wherein X is O or and the one or more protic groups of $R_4$ are selected from the group consisting of OH and $CO_2H$.

16. The resin of claim 14, wherein the acrylic compound is a member of the group consisting of β-hydroxyethyl methacrylate and t-butylaminoethyl methacrylate.

17. The resin of claim 14, wherein the hydroxylated acrylic compound is a combination of 2,2-bis-(4-(2'-hydroxy-3'-methacryloxypropoxy) phenyl)propane and β-hydroxyethyl methacrylate.

18. The resin of claim 14, wherein the tetraalkoxysilane is tetraethoxysilane and the dialkoxysilane is 3-methacryloxypropylmethyldimethoxysilane.

19. The resin of claim 14, wherein the silane is tetraethoxysilane or 3-methacryloxypropylmethyldimethoxysilane.

20. The resin of claim 14, wherein the hydroxylated acrylic compound is β-hydroxyethyl methacrylate.

21. The resin of claim 18, wherein the hydroxylated acrylic compound is a combination of 2,2-bis-(4-(2'-hydroxy-3'-methacryloxypropoxy)phenyl)propane and β-hydroxyethylmethacrylate.

22. The resin of claim 14, wherein the animated acrylic compound is t-butylaminoethyl methacrylate.

23. A silylated resin represented by the general formula (I):

(I)

in which:
R$_1$ is an aliphatic, cycloaliphatic, aryl, hydrocarbon, or fluorocarbon group;
R$_2$ is the same as R$_1$ or a different aliphatic, cycloaliphatic, aryl, hydrocarbon, or fluorocarbon group;
X is O, NCH$_3$ or M$_1$ is where R$_3$ is H, CH$_3$, or CH$_2$CH$_3$;
M$_2$ is the same as M$_1$ or a different functional or non-functional group selected from the group consisting of:

CF$_3$, and C$_6$H$_5$;
n is 1–3;
x is 1–20; and
y is 1–20.

24. The resin of claim 23, wherein X is O or

* * * * *